United States Patent [19]

Beisswenger et al.

[11] Patent Number: 5,994,393
[45] Date of Patent: Nov. 30, 1999

[54] ALPHA-LIPOIC ACID WITH NOVEL MODIFICATION

[75] Inventors: Thomas Beisswenger, Radebeul; Gunter Laban, Langebrück; Karl-Friedrich Landgraf; Eberhard Oestreich, both of Dresden; Matthias Rischer, Frankfurt, all of Germany

[73] Assignee: ASTA Medica Aktiengesellschaft, Dresden, Germany

[21] Appl. No.: 09/074,645

[22] Filed: May 8, 1998

[51] Int. Cl.⁶ ....................................................... A01N 43/26
[52] U.S. Cl. .............................................. 514/440; 549/39
[58] Field of Search ................................ 549/39; 514/440

[56] References Cited

U.S. PATENT DOCUMENTS 5,455,264  10/1995  Beisswenger et al. ................. 514/440

*Primary Examiner*—Dwayne C. Jones
*Attorney, Agent, or Firm*—Pillsbury Madison & Sutro LLP

[57] ABSTRACT

The invention is relative to a thioctic acid with a predominant amount of an enantiomer and a novel modification, in the case of which the X-ray powder diffractograms show a characteristic reflex in the range of 23.4 to 22.7° 2 theta(Cu) which shifts in the direction of the smaller angular values as the enantiomer content increases.

8 Claims, 5 Drawing Sheets

ALPHA-LIPOIC ACID WITH NOVEL MODIFICATION

BACKGROUND OF THE INVENTION

1. Field of the Invention

Alpha-lipoic acid is used in pharmaceutical formulations both in infusion solutions as well as in solid galenic formulations for oral use. Synthetically produced, racemic DL-alpha-lipoic acid, also designated as RS-thioctic acid, is used for this.

2. Background Information

An enantiomer of alpha-lipoic acid, R-thioctic acid, occurs as natural substance in practically all animal and vegetable cells. R-thioctic acid is of essential significance as coenzyme in the oxidative decarboxylation of alpha-keto acids (e.g. pyruvic acid). Thioctic acid is pharmacologically active and exhibits antiphlogistic and antinoceceptive (analgetic) as well as cytoprotective properties. An important medical indication is the treatment of diabetic polyneuropathy. Furthermore, thioctic acid is used in cosmetics as well as in the supplementation of nutrition, e.g. on account of its antioxidative action. The use of R-thioctic acid appears to be especially advantageous thereby since it is present in a form identical to nature (see also EP 0,572,922 A1) and is inserted only in the natural form as cofactor into the pyruvate-dehydrogenase complex (Oehring et al., Biol. Chem. Hoppe-Seyler 373, 333–335, 1992). According to recent results (Baur et al., Klin. Wochenschr. 1991, 69(15), 722–4) thioctic acid can possibly become significant in the combating of disease caused by HIV-1- and HTLV IIIB viruses.

In the case of the pure, optical isomers of thioctic acid (R and S form, that is, R-thioctic acid and S-thioctic acid), in contrast to the racemate the R enantiomer is primarily antiphlogistically and the S enantiomer primarily antinociceptively active (see also EP 0,427,247 A2). Therefore, in order to achieve a selective action the production and use of the pure enantiomers are of great importance.

A number of methods are known for the purposeful production of the pure enantiomers of R- or S-thioctic acid which methods generally contain an enantioselective synthesis stage for the production of a suitable chiral precursor or intermediate stage. All previously known methods require a high synthetic expense and exertions to deplete the undesired enantiomer and have up to the present not made an industrialscale use possible.

The melting range of the pure enantiomers of thioctic acid (47 to 49° C.) is lower compared to the racemic compound (58–61° C.). In the production of solid galenic formulations, which generally takes place under pressing or compacting, the use of pressure on the material is indispensable so that on the one hand a heating and on the other hand a melting of the thioctic acid takes place. Concentrated solutions of thioctic acid or its melts polymerize immediately and can no longer be converted into a crystalline form by cooling.

This effect is very pronounced in the case of pure enantiomers of thioctic acid due to the low melting point. The use of basic salts has been suggested for the desirable therapeutic use of the pure enantiomers (see also EP 702,953 A2).

SUMMARY OF THE INVENTION

The present invention has the problem of producing thioctic acid which contains the desired enantiomer in an enriched fashion and on the other hand of finding a modification or form which behaves to the greatest extent possible like racemic thioctic acid during its processing on account of its physical properties.

If an enantiomer is already present in an enriched but not yet pure form during the production of thioctic acid by a suitable synthetic production method a thioctic acid is surprisingly obtained during the crystallization from suitable solvents which contains the predominant enantiomer in enriched form but does not behave like the corresponding solid mixtures of the crystalline racemate with pure crystalline R- or S-thioctic acid. The novel modification formed has an X-ray powder diffractogram which neither corresponds to that of the racemate nor that of the pure enantiomers or of their mixtures.

BRIEF DESCRIPTION OF THE DRAWINGS

The present invention is relative to thioctic acid with a predominant amount of one enantiomer, preferably with an enantiomeric ratio of 60:40 to 97:3, which is present in a novel modification. FIG. 3 shows a thioctic acid with an amount of R-enantiomer of 66% and 34% S-enantiomer, FIG. 4 shows one with an amount of R-enantiomer of 76% and 24% S-enantiomer and FIG. 5 shows a thioctic acid with an amount of R-enantiomer of 95% with 5% S-enantiomer.

DETAILED DESCRIPTION OF THE INVENTION

Figure 1:
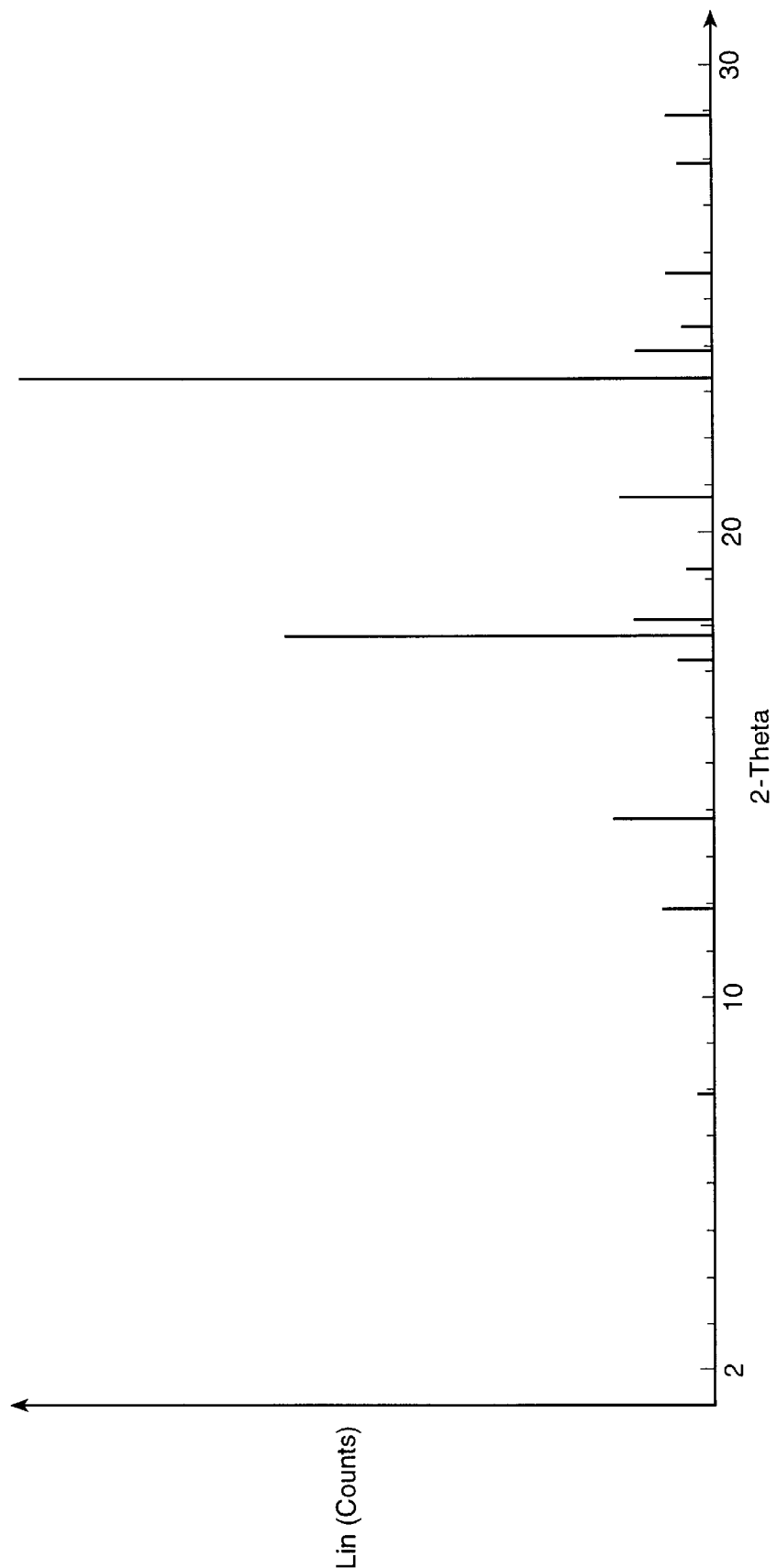
FIGS. 1 and 2 show the typical X-ray diffractogram pictures, known in the literature, of racemic RS-thioctic acid as well as of pure R-thioctic acid. Furthermore.
Figure 2:
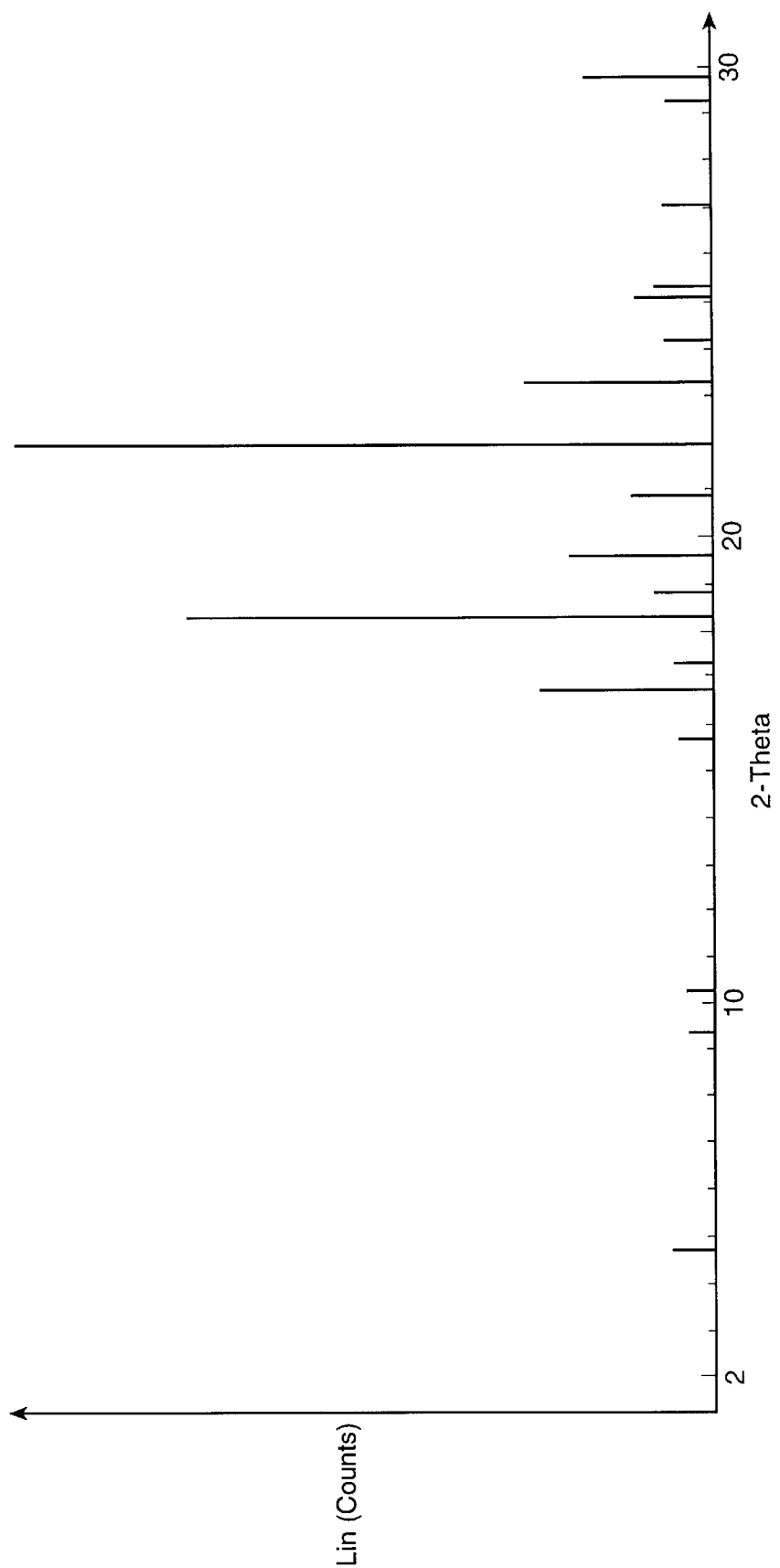
Figure 3:
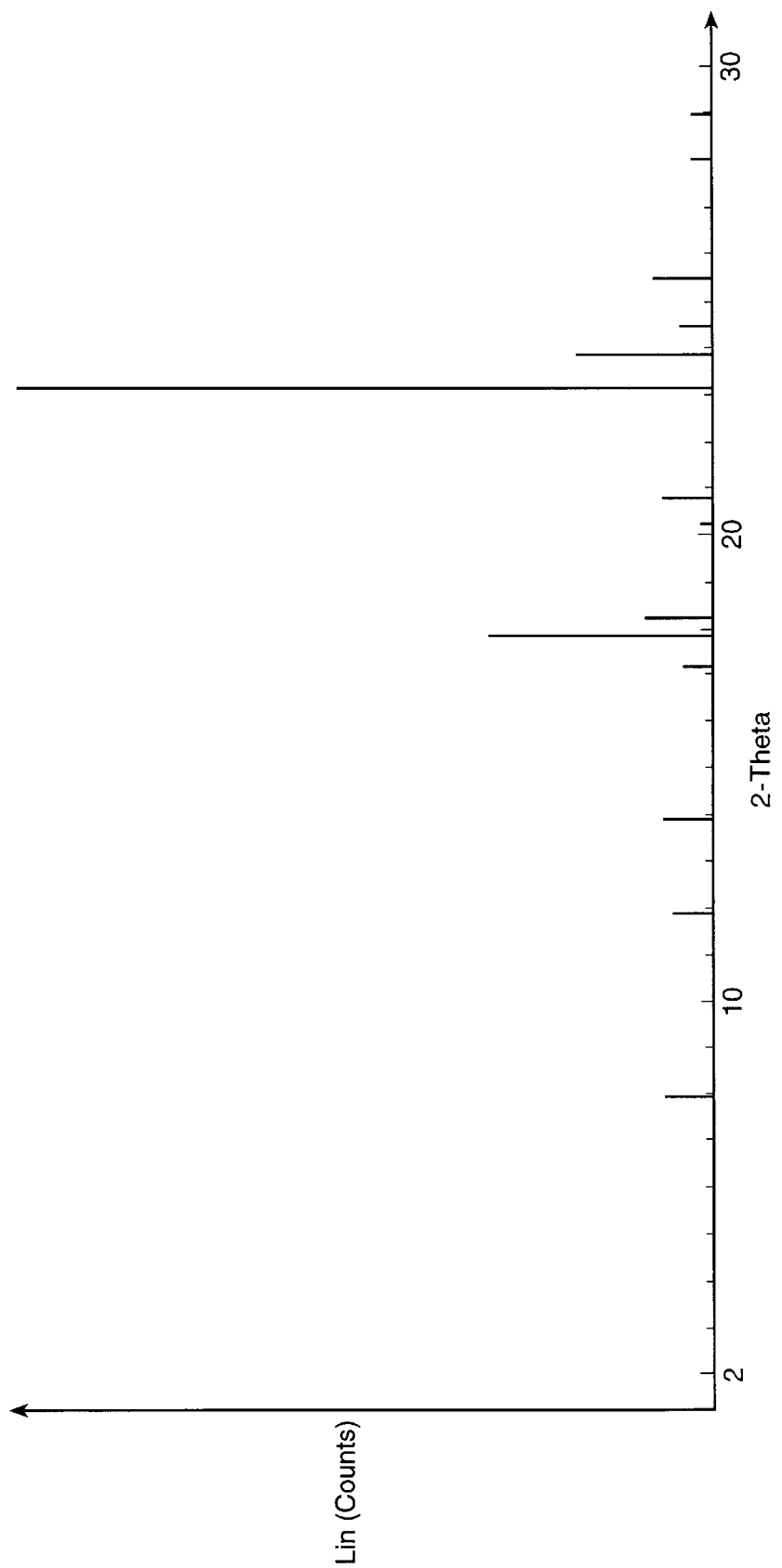
FIGS. 3 to 5 show X-ray powder diffractograms stemming from crystallized thioctic acid produced from solutions of thioctic acid enriched with pure enantiomers.
Figure 4:
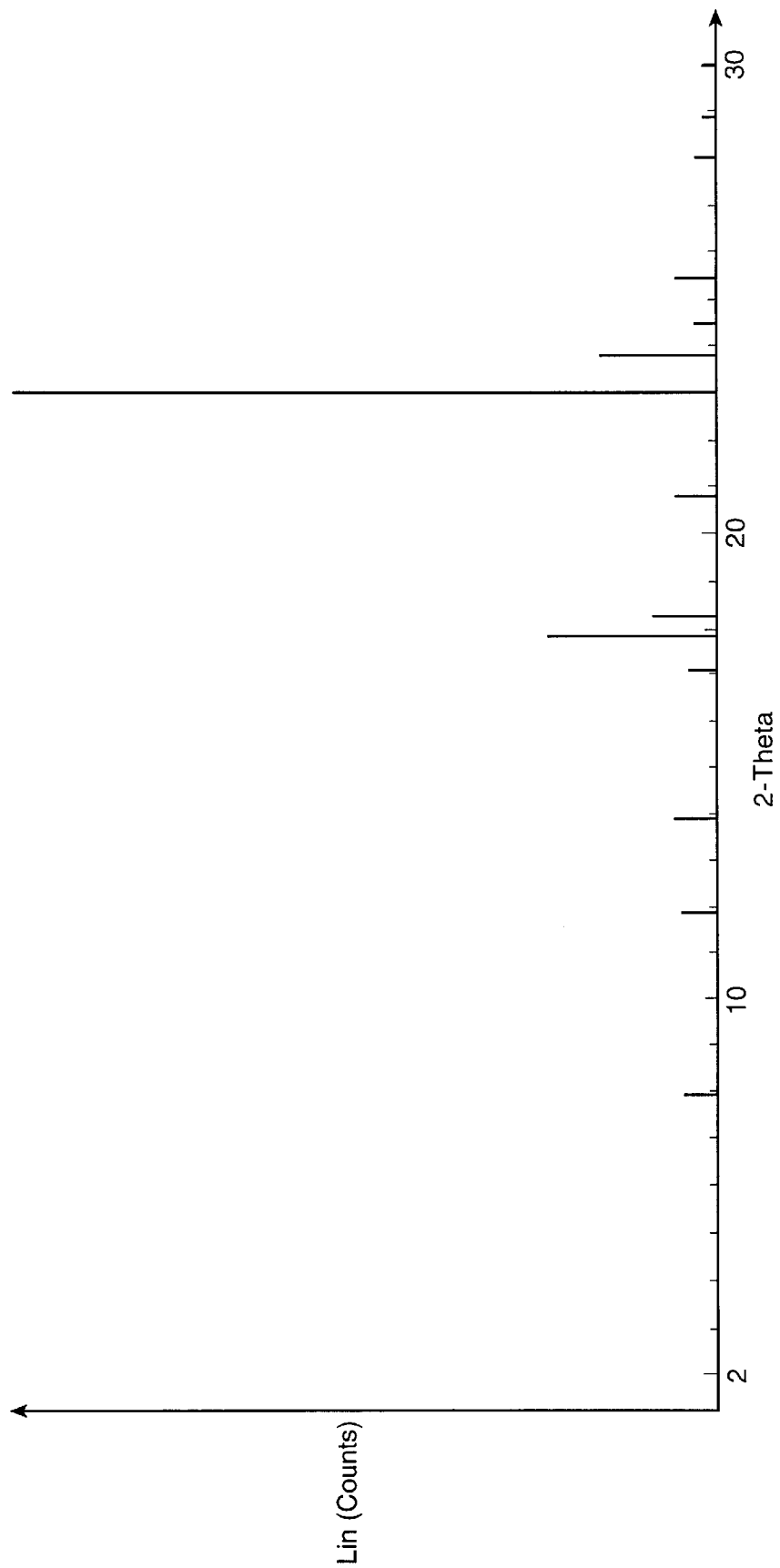
Figure 5:
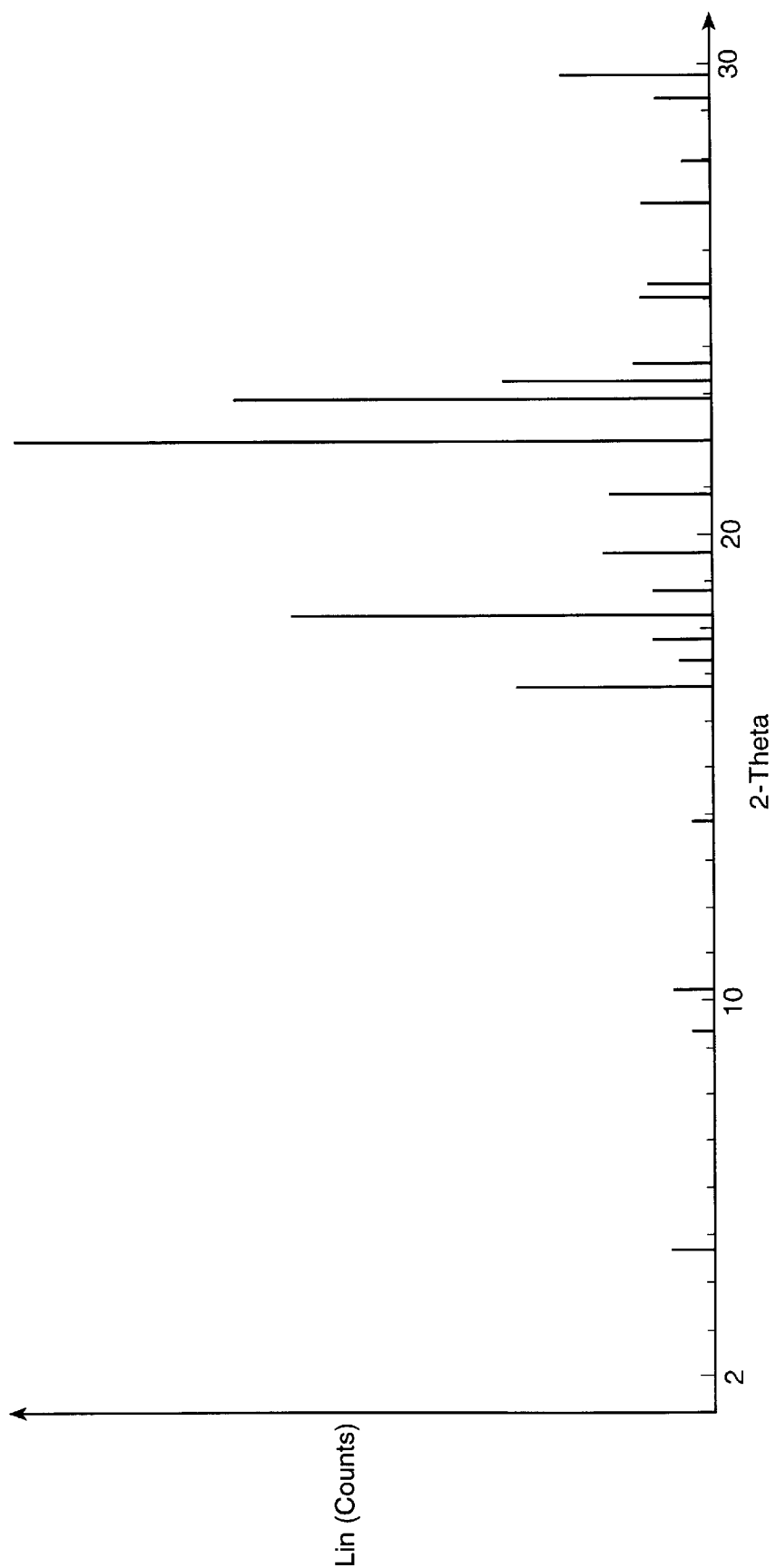

The thioctic acid of the invention surprisingly exhibits a melting range of 48 to 59° C., which deviates from the expected eutectic melting range of 44 to 48° C. Furthermore, it makes possible a preferred galenic processing and has a better temperature stability than the pure enantiomer.

The crystallization of thioctic acid can be carried out in a suitable organic solvent. Examples of organic solvents, which can also contain water, are, among others, aliphatic hydrocarbons with a carbon chain length between 3 and 10 carbon atoms, aromatic hydrocarbons which are liquid, esters from aliphatic or cycloaliphatic carboxylic acids with 2 to 6 carbon atoms and aliphatic or cycloaliphatic alcohols with 1 to 6 carbon atoms, aliphatic or cycloaliphatic alcohols with 1 to 6 carbon atoms [sic], ethers and glycol ethers [glymes] or homogenous mixtures of the cited solvents. Especially preferred solvents are ethyl acetate, hexane, cyclohexane, pentane, heptane, diisopropyl ether, toluene, ethanol and their homogeneous mixtures.

The purity and composition of the thioctic acids obtained were determined by analysis on a chiral HPLC column. The determination of the melting range took place by means of differential scanning calorimetry (DSC) with a heating rate of 2° K/min. The present invention makes it possible to make accessible for various applications the enantiomers of thioctic acid in enriched form, which can be obtained in a crystalline and pure form in a simple and economic manner from solutions of the same.

The invention is explained in detail in the following examples.

EXAMPLE 1

41.2 g racemic thioctic acid were dissolved in a mixture of 960 ml cyclohexane and 240 ml ethyl acetate at 40° C.

and subsequently 12.0 g (100 mmol) S-(−)-α-methylbenzylamine slowly added dropwise. The mixture was then cooled down to 25° C., the precipitate removed by suction and post-washed with a cyclohexane-ethyl acetate mixture. 660 ml water were added to the filtrate and a pH of 1–1.5 adjusted at room temperature with approximately 10% hydrochloric acid. The phases were separated and the aqueous phase re-extracted with 60 ml of a cyclohexane-ethyl acetate mixture. The combined organic phases were distilled under a vacuum to approximately ⅕ of the original volume. The distillation residue obtained was cooled off to −5° to −10° C. and agitated for crystallization. The precipitate was filtered off, washed and dried. 20.4 g thioctic acid were obtained in the novel modification as first crystallizate. The R-(+)-thioctic acid content was 69.0%.

EXAMPLE 2

A solution which contained 20.0 g R-(+)-thioctic acid and 5.0 g S-(−)-thioctic acid in a mixture of 225 ml cyclohexane and 25 ml ethyl acetate was cooled off from 35 to 40° C. down to −5 to −10° C., filtered and dried. 17.3 g thioctic acid were obtained in the novel modification as first crystallizate. The R-(+)-thioctic acid content was 75.6% with a melting range of 49 to 54° C.

EXAMPLE 3

A solution which contained 11.7 g R-(+)-thioctic acid and 5.0 g S-(−)-thioctic acid in a mixture of 225 ml cyclohexane and 25 ml ethyl acetate was cooled off from 35 to 40° C. down to −5 to −10° C., filtered and dried. 12.0 g thioctic acid were obtained in the novel modification as first crystallizate. The R-(+)-thioctic acid content was 65.8% with a melting range of 54 to 58° C.

EXAMPLE 4

A solution which contained 95.0 g R-(+)-thioctic acid and 5.0 g S-(−)-thioctic acid in a mixture of 225 ml cyclohexane and 25 ml ethyl acetate was cooled off from 35 to 40° C. down to −5 to −10° C., filtered and dried. 87.1 g thioctic acid were obtained in the novel modification as first crystallizate. The R-(+)-thioctic acid content was 93.5% with a melting range of 45 to 47° C.

EXAMPLE 5

A solution which contained 4.0 g R-(+)-thioctic acid and 16.0 g S-(−)-thioctic acid in 80 ml diisopropyl ether was cooled off from 35 to 40° C. down to −5 to −10° C., filtered and dried. 14.5 g thioctic acid were obtained in the novel modification as first crystallizate. The S-(−)thioctic acid content was 75.8% with a melting range of 50 to 56° C.

EXAMPLE 6

A solution which contained 16.6 g R-(+)-thioctic acid and 3.4 g S-(−)-thioctic acid in 80 ml diisopropyl ether was cooled off from 35 to 40° C. down to −5 to −10° C., filtered and dried. 13.5 g thioctic acid were obtained in the novel modification as first crystallizate. The R-(+)thioctic acid content was 78.8% with a melting range of 48 to 54° C.

EXAMPLE 7

A solution which contained 17.5 g R-(+)-thioctic acid and 2.5 g S-(−)-thioctic acid in a mixture of 200 ml n-hexane and 57 ml ethyl acetate was cooled off from 35 to 40° C. down to −5 to −10° C., filtered and dried. 13.5 g thioctic acid were obtained in the novel modification as first crystallizate. The R-(+)-thioctic acid content was 82.6% with a melting range of 47 to 52° C.

EXAMPLE 8

A solution which contained 19.5 g R-(+)-thioctic acid and 0.5 g S-(−)-thioctic acid in a mixture of 24 ml toluene and 6 ml n-heptane was cooled off from 35 to 40° C. down to −5 to −10° C., filtered and dried. 13.0 g thioctic acid were obtained in the novel modification as first crystallizate. The R-(+)-thioctic acid content was 94.5% with a melting range of 45 to 48° C.

EXAMPLE 9

A solution which contained 3.0 g R-(+)-thioctic acid and 7.0 g S-(−)-thioctic acid in a mixture of 135 ml cyclohexane and 15 ml ethyl acetate was cooled off from 35 to 40° C. down to −5 to −10° C., filtered and dried. 8.5 g thioctic acid were obtained in the novel modification as first crystallizate. The S-(−)-thioctic acid content was 67.8% with a melting range of 53 to 58° C.

What is claimed is:

1. Crystalline thioctic acid comprising the enantiomers R-thioctic acid and S-thioctic acid, said enantiomers being present in unequal proportions between 60/40 and 97/3, wherein X-ray powder diffractograms of said thioctic acid have a characteristic reflex in the range of 23.4 to 22.7° 2 theta(Cu) which shifts in the direction of smaller angular values as the difference in proportions is greater.

2. The thioctic acid of claim 1 containing between 60 and 97% R-thioctic acid.

3. The thioctic acid of claim 1 containing between 60 and 97% S-thioctic acid.

4. The thioctic acid according to one of claims 1–3 having a melting point between 48 and 59° C.

5. A method of producing crystalline thioctic acid according to claim 1 comprising the steps of
   i) providing a solvent containing R-thioctic acid and S-thioctic acid in proportions between 60/40 and 97/3, said solvent being selected from the group consisting of an aliphatic hydrocarbon with a chain length of 3–10 carbon atoms, a liquid aromatic hydrocarbon, an ester of an aliphatic or cycloaliphatic carboxylic acid with 2–6 carbon atoms, and an aliphatic or cycloaliphatic alcohol with 2–6 carbon atoms, and homogeneous mixtures thereof; and
   ii) crystallizing out said thioctic acid.

6. The method of claim 5 wherein the solvent is selected from the group consisting of ethyl acetate, hexane, cyclohexane, pentane, heptane, diisopropyl ether, toluene, ethanol and homogeneous mixtures thereof.

7. The method of claim 5 or 6, wherein the solvent additionally contains water.

8. A pharmaceutical composition consisting essentially of crystalline thioctic acid comprising the enantiomers R-thioctic acid and S-thioctic acid, said enantiomers being present in unequal proportions between 60/40 and 97/3, wherein X-ray powder diffractograms of said thioctic acid have a characteristic reflex in the range of 23.4 to 22.7° 2 theta(Cu) which shifts in the direction of smaller angular values as the difference in proportions is greater, and pharmaceutically acceptable auxiliary substances.

* * * * *